(12) United States Patent
Mohe et al.

(10) Patent No.: US 8,846,614 B2
(45) Date of Patent: Sep. 30, 2014

(54) PROCESS FOR THE SYNTHESIS OF 37-MER PEPTIDE PRAMLINTIDE

(75) Inventors: Nikhil Umesh Mohe, Maharashtra (IN); Praful Shamrao Chavre, Maharashtra (IN); Bharti Prabhakarrao Deshmukh, Maharashtra (IN); Chandrakesan Muralidharan, Maharashtra (IN); Lester John Lobo, Maharashtra (IN); Digamber Shripati Pawar, Maharashtra (IN); Divya Lal Saksena, Maharashtra (IN)

(73) Assignee: USV Limited (IN)

( * ) Notice: Subject to any disclaimer, the term of this patent is extended or adjusted under 35 U.S.C. 154(b) by 0 days.

(21) Appl. No.: 13/591,647

(22) Filed: Aug. 22, 2012

(65) Prior Publication Data

US 2013/0109622 A1 May 2, 2013

(30) Foreign Application Priority Data

Aug. 25, 2011 (IN) .......................... 2382/MUM/2011

(51) Int. Cl.
- *A61K 38/00* (2006.01)
- *C07K 14/00* (2006.01)
- *C07K 14/575* (2006.01)
- *C07K 1/04* (2006.01)
- *C07K 14/01* (2006.01)

(52) U.S. Cl.
CPC . *C07K 1/04* (2013.01); *A61K 38/00* (2013.01); *C07K 14/575* (2013.01); *C07K 14/01* (2013.01)
USPC .......................................... 514/6.9; 530/324

(58) Field of Classification Search
CPC .................................................... C07K 14/00
See application file for complete search history.

(56) References Cited

U.S. PATENT DOCUMENTS

| | | | |
|---|---|---|---|
| 5,424,394 A * | 6/1995 | Lehman de Gaeta et al. | 530/324 |
| 5,998,367 A * | 12/1999 | Gaeta et al. | 514/6.8 |
| 2008/0287650 A1* | 11/2008 | Tovi et al. | 530/317 |

FOREIGN PATENT DOCUMENTS

WO  WO 2009003666 A1 * 1/2009

OTHER PUBLICATIONS

Dolling et al., J. Chem. Soc., Chem. Commun., 1994, 853-854.*
Wohr et al., J. Am. Chem. Soc., 1996, 118, 9218-9227.*
Supports for Solid Phase Synthesis, Biosearch Tech. Inc., Price List, Jan. 2001.*
Novabiochem, "Guidelines for the use of Pseudoproline Dipeptides", published on 2004, also in the IDS dated Aug. 22, 2012.*
Coin et al., Nature Protocols, 2007, vol. 2, No. 12, 3247-3256.*
"Novabiochem®—Guidelines for the use of Pseudoproline Dipeptides", innovations 1/04, (2004), 2 pgs.
Adedini, A., et al., "Incorporation of Pseudoproline Derivatives Allows the Facile Synthesis of Human IAPP, a Highly Amyloidogenic and Aggregation-Prone Polypeptide", *Organic Letters*, 7(4), (2005), 693-696.
Coic, Y.-M., et al., "Slighthly modifying pseudoproline dipeptides incorporating strategy enables solid phase synthesis of a 54 AA fragment of caveolin-1 encompassing the intramembrane domain", *Journal of Peptide Science*, 16, (2010), 98-104.
Garcia-Martin, F., et al., "The Synergy of ChemMatrix Resin® and Pseudoproline Building Blocks Renders RANTES, A Complex Aggregated Chemokine", *Biopolymers (Peptide Science)*, vol. 84, (2006), 566-575.
Keller, M., et al., "Enchancing the Proline Effect: Pseudo-Prolines for Tailoring Cis/Trans Isomerization", *J. Am. Chem. Soc.*, 120, (1998), 2714-2720.
Page, K., et al., "Fast Fmoc synthesis of hAmylin$_{1-37}$ with pseudoproline assisted on-resin disulfide formation", *Journal of Peptide Science*, 13, (2007), 833-838.
Ruckle, T., et al., "Pseudo-Prolines in Cyclic Peptides : Conformational Stabilisation of cyclo[Pro-Thr( Me,Me pro)-Pro]", *Tetrahedron*, 55, (1999), 11281-11288.
Valente, A. P., et al., "Study of the effect of the peptide loading and solvent system in SPPS by HRMAS-NMR", *Journal of Peptide Science*, 11, (2005), 556-563.
White, P., et al., "Expediting the Fmoc Solid Phase Synthesis of Long Peptides Through the Application of Dimethyloxazolidine Dipeptides", *Journal of Peptide Science*, 10, (2004), 18-26.
Wohr, T., et al., "Pseudo-Prolines as a Solubilizing, Structure-Disrupting Protection Technique in Peptide Solutions", *J. Am. Chem. Soc.*, 118, (1996), 9218-9227.

* cited by examiner

*Primary Examiner* — Marcela M Cordero Garcia
*Assistant Examiner* — Kaipeen Yang
(74) *Attorney, Agent, or Firm* — Schwegman Lundberg & Woessner, P.A.

(57) ABSTRACT

A process for the production of pramlintide, a 37-mer peptide, is provided. The synthesis provides a high yield synthesis of the peptide in relatively pure form. Further purification can be achieved by preparative HPLC.

7 Claims, 5 Drawing Sheets

PROCESS FOR THE SYNTHESIS OF 37-MER PEPTIDE PRAMLINTIDE

CROSS-REFERENCE TO RELATED APPLICATIONS

This application claims the priority of Indian Patent Application No. 2382/MUM/2011, the disclosure of which in incorporated herein by reference in its entirety.

FIELD OF THE INVENTION

The invention relates to a novel solid phase peptide synthesis of a 37-mer amyloid peptide, Pramlintide, and intermediates thereof. More particularly the invention relates to the surprising finding of use of a single pseudoproline moiety for the synthesis of Pramlintide giving higher purity as compared to the use of more than one pseudoproline moieties. Further the invention also relates to a surprising finding of improvement in purity of the crude peptide by modifying the deprotection solvent system in addition to the incorporation of a single pseudoproline moiety.

BACKGROUND

Amylin is a 37-mer aminoacid peptide hormone that is produced in the pancreas and co-secreted with insulin in response to serum glucose levels. Pramlintide is a synthetic analog of amylin ($^{25,28,29}$tri-L-proline amylin) that retains the biological activity of the hormone while offering superior physical and chemical properties that facilitate drug synthesis and development of a stable drug product for parenteral administration. Pramlintide is approved by US FDA for treating people with type 1 and type 2 diabetes.

Amylin contains a disulphide bridge from Cys-2 to Cys-7 and has an amidated C-terminus. During synthesis amylin is prone to aggregation because of excessive hydrophobic tendencies. This causes low coupling yields, incomplete couplings and side products. The addition of pseudoproline dipeptides to the peptide increases the purity of difficult peptides by decreasing the aggregation.

The synthetic analog pramlintide was arrived at from amylin by substitution of Ala$^{25}$, Ser$^{28}$ and Ser$^{29}$ with proline residues. The pramlintide sequence contains no free carboxyl groups, even at the amidated C-terminus (tyrosine). All the carboxyl groups in pramlintide are amidated, rendering the molecule cationic (protonated histidine, and arginine) at acidic pH. Pramlintide is isolated as a salt with acetate as the counterion. The peptide sequence is:

(formula 1; SEQ ID NO: 1)

H-Lys-Cys-Asn-Thr-Ala-Thr-Cys-Ala-Thr-Gln-Arg-Leu-

Ala-Asn-Phe-Leu-Val-His-Ser-Ser-Asn-Asn-Phe-Gly-

Pro-Ile-Leu-Pro-Pro-Thr-Asn-Val-Gly-Ser-Asn-Thr-

Tyr-NH$_2$, wherein the line indicates the Cys-Cys disulfide bridge of the bioactive form.

Solid phase peptide synthesis is an alternative to solution phase synthesis. Currently large number of peptides have been successfully produced on a large scale using solid phase peptide synthesis.

Despite having advantages over solution phase synthesis, sometimes the synthesis process becomes highly expensive due to the heavy cost incurred by raw materials used for the synthesis for e.g., protected aminoacids, aminoacid derivatives and specific resins. The use of expensive aminoacid derivatives becomes a major setback in the synthesis, as the process becomes very expensive due to which the commercial scale production of the peptide hinders affecting the commercial business gain.

U.S. Pat. No. 5,686,411 discloses the solid phase synthesis of amylin and amylin analogs using methylbenzhydrylamine anchor-based resin and Nα-Boc/benzyl-side chain protection. Also it discloses the method of treating diabetes mellitus.

U.S. Pat. No. 5,424,394 discloses a solid phase peptide synthesis of amylin or amylin analogs using classical stepwise process wherein such synthetic human amylin is substantially free of deletion and other contaminating peptides having a purity to boat least about 95%. The invention also describes the use of Boc protection and double couplings cycles to get enhanced yield.

As with any drug substance, identifying and quantitating low levels of related substance impurities present in synthesis lots warrants a robust manufacturing process for pramlintide. Missed couplings, double-couplings, and L- to D-aminoacid isomerizations are common errors that occur in peptide synthesis to yield, respectively, single-point aminoacid deletion peptides, addition peptides, and diastereomers as related substances of the desired molecule. Specifically for pramlintide, the 37 aminoacid residue length severely complicates detecting single aminoacid modifications and requires highly selective analytical test methods for purity determinations. Degradation pathways for peptides in acidic aqueous solution frequently involve deamidation at asparagine and glutamine plus hydrolytic backbone cleavage. The 37 aminoacid length and the 8 potential deamidation sites create a potential for many degradation products that differ from pramlintide by modifications at only a single aminoacid. Hence the synthesis of pramlintide poses significant challenge for manufacturers being a difficult peptide to synthesize.

Successful peptide assembly is still hampered by inherent problems such as poor solvation of the growing peptide chain during solid phase synthesis as well as limited solubility of fully protected peptide fragments in the solution approach, often leading to incomplete coupling steps. These undesirable physicochemical problems originate from intermolecular hydrophobic aggregation of the protected peptide chains and/or the formation of secondary structures, most notable β-sheets. Reported attempts to suppress the degenerative effect of such associations during aminoacylation reactions involve essentially "external factors" like solvent composition, elevated temperature, and use of chaotropic salts or solubilizing protecting groups which have been shown to have variable efficiencies. Hydrogen-bonded association has also been prevented by the introduction of an amide protecting group within the peptide chain.

Mutter et al. (1996) were the first to use serine-, threonine-, and cysteine-derived cyclic building blocks (pseudoprolines) to serve as reversible protecting groups for Ser, Thr, and Cys, which have proven to be versatile tools for overcoming some intrinsic problems in the field of peptide chemistry. Mutter et were also the first to report that Ser/Thr-derived oxazolidine and Cys-derived thiazolidine derivatives exert a pronounced effect upon backbone conformation due to their structural similarity with proline itself. Due to the induction of a kink conformation in the peptide backbone, originating in the preference for cis amide bond formation, Ψpro prevent peptide aggregation, self-association, and β-structure formation, thus improving the solvation and coupling kinetics of the growing peptide chain considerably. These building blocks are readily accessible by cyclization Ser, Thr, or Cys with aldehydes or ketones and serve as reversible protecting group in peptide synthesis. As a particular feature, variation of the C-2 substituents directly affects the ring stability, thus allowing for differential chemical stabilities in a variety of synthetic strategies.

Aggregation and hence problems in solid phase synthesis is commonly believed in the art to correlate with occurrence of extended regions of β-sheet structure. A β-sheet structure contents is common to most peptides of at least 10 aminoacids length and do not correlate with any unusual problem in synthetic methodology.

Pseudoproline dipeptides are basically incorporated in the most common peptide synthesis strategies such as a) they can be coupled to growing peptide chains using standard procedures and coupling reagents, b) they are easily cleaved with standard TFA mixtures, and c) they are compatible with synthesis strategies involving Fmoc and Z-aminoacids.

PCT publication WO2009003666 discloses the preparation of Pramlintide via a convergent three fragment synthesis strategy from the fragments comprising the aminoacid residues 1-12, 13-24 and 25-37 respectively. The described procedure uses three pseudoprolines moieties for the synthesis of pramlintide, wherein it improves the solubility of the peptide and prevented or decreased its aggregation.

SUMMARY

The present invention is directed to methods and materials for the solid phase peptide synthesis of the 37-mer pramlintide One aspect of the present invention is a process for the production of pramlintide, a disulfide-bridged peptide of formula (1):

(formula 1; SEQ ID NO: 1)

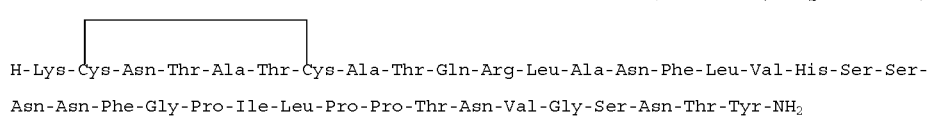

wherein the Cys-Cys line indicates a cystine disulfide bridge;
comprising:
(a) coupling Fmoc-Tyr(X)-OH to an acid-labile resin with a substitution value ranging from 0.15-0.60 mmol/g, to provide a sidechain-protected resin-bound tyrosine residue, Fmoc-Tyr(X)-Resin; then,
(b) removing the N-terminal Fmoc protecting group thereof using piperidine in 1-hydroxybenzotriazole (HOBt) in polar aprotic solvent to provide an N-terminal free amino group; then,
(c) assembling each respective Fmoc-protected aminoacid residue sequentially C-terminal to N-terminal under conditions suitable for peptide coupling, to provide sidechain-protected resin-bound peptide of the formula (2RBP):
Fmoc-Asn(Y)-Asn(Y)-Phe-Gly-Pro-Ile-Leu-Pro-Pro-Thr(X)-Asn(Y)-Val-Gly-Ser(X)-Asn(Y)-Thr(X)-Tyr(X)-Resin (SEQ ID NO:2);
wherein (X) and (Y) signify acid-labile sidechain protecting groups, wherein (X) can be removed under acidic conditions to yield a free OH group and (Y) can be removed under acidic conditions to yield a free NH or SH group; then,
(d) removing the N-terminal Fmoc group using piperidine in 1-hydroxybenzotriazole (HOBt) in polar aprotic solvent to provide an N-terminal free amino group; then,
(e) coupling Fmoc-Ser(X)-Ser($\Psi^{Me,Me}$ Pro)-OH to the N-terminal free amino group, under conditions suitable for peptide coupling, wherein Ser($\Psi^{Me,Me}$ Pro) signifies a pseudoproline serine-derived oxazolidine of formula

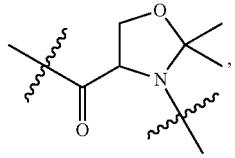 [SMILES: *C(=O)C1COC(C)(C)N1*]

wherein each wavy line indicates a point of bonding in the peptide chain, to yield a sidechain-protected resin-bound peptide of Formula (3RBP):
Fmoc-Ser(X)-Ser($\Psi^{Me,Me}$ Pro)-Asn(Y)-Asn(Y)-Phe-Gly-Pro-Ile-Leu-Pro-Pro-Thr(X)-Asn(Y)-Val-Gly-Ser(X)-Asn(Y)-Thr(X)-Tyr(X)-Resin (SEQ ID NO:3); then,
(f) further assembling each respective Fmoc-protected aminoacid residue sequentially C-terminal to N-terminal, under conditions suitable for stepwise N-terminal Fmoc removal and peptide coupling, to the sidechain-protected resin-bound peptide of formula (3RBP), to provide a sidechain-protected resin-bound peptide of formula (4RBP):
Fmoc-Lys(Boc)-Cys(Y)-Asn(Y)-Thr(X)-Ala-Thr(X)-Cys(Y)-Ala-Thr(X)-Gln(Y)-Arg(Pbf)-Leu-Ala-Asn(Y)-Phe-Leu-Val-His(Y)-Ser(X)-Ser($\Psi^{Me,Me}$ Pro)-Asn(Y)-Asn(Y)-Phe-Gly-Pro-Ile-Leu-Pro-Pro-Thr(X)-Asn(Y)-Val-Gly-Ser(X)-Asn(Y)-Thr(X)-Tyr(X)-Resin (SEQ ID NO:4);
with a purity of crude peptide of ≥30%; then,
(g) sidechain-deprotecting and cleaving a 37-mer cysteine-reduced peptide of Formula (4) from the resin by contacting with acid:
H-Lys-Cys-Asn-Thr-Ala-Thr-Cys-Ala-Thr-Gln-Arg-Leu-Ala-Asn-Phe-Leu-Val-His-Ser-Ser-Asn-Asn-Phe-Gly-Pro-Ile-Leu-Pro-Pro-Thr-Asn-Val-Gly-Ser-Asn-Thr-Tyr-Nh$_2$ (formula (4); SEQ ID NO:5); then,
(h) oxidizing the peptide of formula (4) to the disulfide-bridged peptide of Formula (1), and,
(i) purifying the peptide of formula (4), or the peptide of formula (1), or optionally both, by RP-HPLC.

Another aspect of the invention is the sidechain-protected resin-bound peptide of Formula (4RBP):
Fmoc-Lys(Boc)-Cys(Y)-Asn(Y)-Thr(X)-Ala-Thr(X)-Cys(Y)-Ala-Thr(X)-Gln(Y)-Arg(Pbf)-Leu-Ala-Asn(Y)-Phe-Leu-Val-His(Y)-Ser(X)-Ser($\Psi^{Me,Me}$ Pro)-Asn(Y)-Asn(Y)-Phe-Gly-Pro-Ile-Leu-Pro-Pro-Thr(X)-Asn(Y)-Val-Gly-Ser(X)-Asn(Y)-Thr(X)-Tyr(X)-Resin (SEQ ID NO:4); wherein (X), (Y), Ser($\Psi^{Me,Me}$ Pro), and Resin are as described above.

Still another aspect of the invention is a specific embodiment of the sidechain-protected resin-bound peptide of Formula (4RBP), a sidechain-protected resin-bound peptide of Formula (5RBP):
Fmoc-Lys(Boc)-Cys(Trt)-Asn(Trt)-Thr(tBu)-Ala-Thr(tBu)-Cys(Trt)-Ala-Thr(tBu)-Gln(Trt)-Arg(Pbf)-Leu-Ala-Asn(Trt)-Phe-Leu-Val-His(Trt)-Ser(tBu)-Ser($\Psi^{Me,Me}$ Pro)-Asn(tBu)-Asn(Trt)-Phe-Gly-Pro-Ile-Leu-Pro-Pro-Thr(tBu)-Asn(Trt)-Val-Gly-Ser(tBu)-Asn(Trt)-Thr(tBu)-Tyr(tBu)-Resin (SEQ ID NO:6); wherein Ser($\Psi^{Me,Me}$ Pro) and Resin are as described above.

Another aspect of the present invention the sidechain-protected resin-bound peptide fragment of Formula (3RBP):
Fmoc-Ser(X)-Ser($\Psi^{Me,Me}$ Pro)-Asn(Y)-Asn(Y)-Phe-Gly-Pro-Ile-Leu-Pro-Pro-Thr(X)-Asn(Y)-Val-Gly-Ser(X)-Asn(Y)-Thr(X)-Tyr(X)-Resin (SEQ ID NO:3); wherein (X), (Y), Ser($\Psi^{Me,Me}$ Pro), and Resin are as described above.

A specific embodiment of the sidechain-protected resin-bound peptide fragment of Formula (3RBP) is Fmoc-Ser(tBu)-Ser($\Psi^{Me,Me}$ Pro)-Asn(tBu)-Asn(Trt)-Phe-Gly-Pro-Ile-Leu-Pro-Pro-Thr(tBu)-Asn(Trt)-Val-Gly-Ser(tBu)-Asn(Trt)-Thr(tBu)-Tyr(tBu)-Resin (SEQ ID NO:8), wherein Ser($\Psi^{Me,Me}$ Pro) and Resin are as defined above.

DETAILED DESCRIPTION

Figure 1:
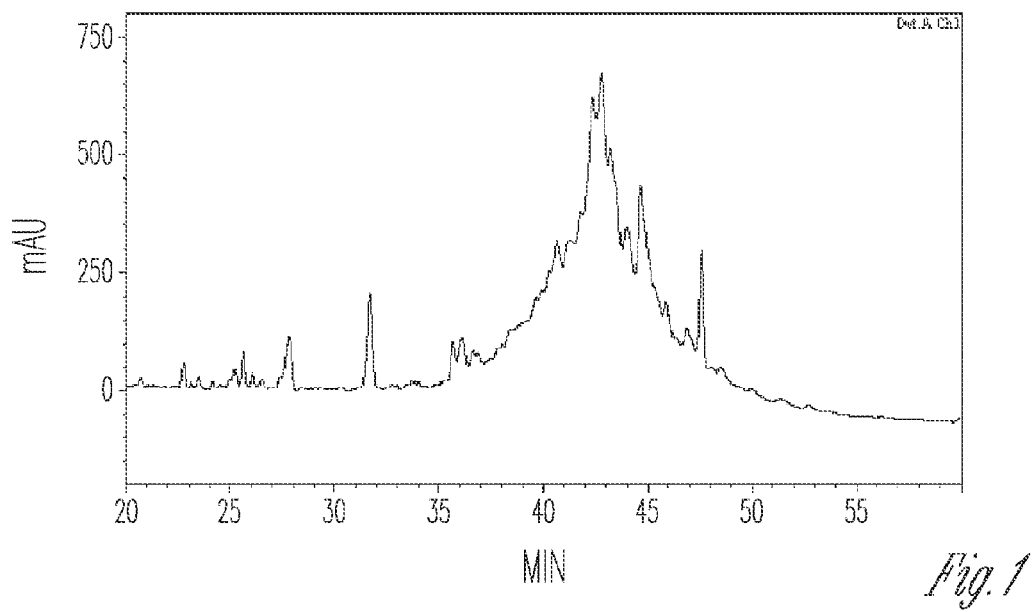
FIG. 1 is an RP-HPLC chromatogram of crude cleavage mixture of Pramlintide (linear reduced form) synthesized using high loading Fmoc-Rink amide AM resin.

It is an object of the present invention to provide a more efficient synthesis of pramlintide that overcomes the known drawbacks of solid phase peptide synthesis and is suitable for the production on an industrial scale. The object has been achieved by the synthesis as disclosed and claimed here.

The methods of solid phase peptide synthesis (SPPS) are well known to the person of ordinary skill in the art in the present invention, the overall synthetic approach was the use of N-terminally Fmoc (fluorenylmethyloxycarbonyl) protected aminoacid residues, that can be deblocked using a base such as piperidine to provide a reactive N-terminal amino group. Sidechain protection is accomplished using (other than the below-described use of a so-called "$\Psi$-proline" heterocycle for sidechain protection of serine, providing unexpectedly advantageous results in terms of yield and purity) acid-labile sidechain blockers such as are well-known in the art, such as tert-butyl (tBu), trityl (Trt), and the like. Upon cleavage of the sidechain-protected, resin-bound peptide fragment from the resin along with side-chain deprotection, the two cysteine residue thiol groups are then oxidized to form the cyclic disulfide-bridged cystine-comprising pramlintide.

To summarize the SPPS methods used herein, the carboxy-terminal aminoacid residue Tyr, bearing acid-labile sidechain protection that can release an OH group upon removal (designated an (X) protecting group herein), e.g., a tBu (tert-butyl) group, is bound to the porous resin (typically a plurality of beads). As is well-known in the art, the structural chemistry of the resin can be used to control the C-terminal chemistry of the resulting peptide upon acid-catalyzed release from the resin. For example, some resins are adapted to yield a free carboxylic acid group upon cleavage of the final peptide chain from the solid support; other resins are adapted to yield a C-terminal carboxamide group (primary amide $CONH_2$) upon cleavage. In the present inventive synthesis of pramlintide, formula (1):

(formula 1; SEQ ID NO: 1)

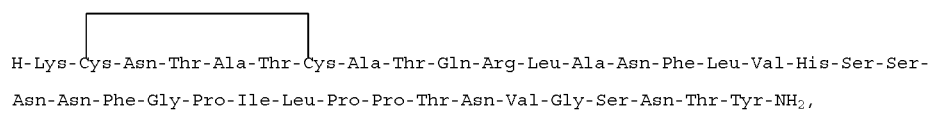

H-Lys-Cys-Asn-Thr-Ala-Thr-Cys-Ala-Thr-Gln-Arg-Leu-Ala-Asn-Phe-Leu-Val-His-Ser-Ser-Asn-Asn-Phe-Gly-Pro-Ile-Leu-Pro-Pro-Thr-Asn-Val-Gly-Ser-Asn-Thr-Tyr-$NH_2$, as disclosed and claimed herein, a C-terminal carboxamido group is desired, so a resin yielding the C-terminal carboxamido group is selected by the person of skill for conducting the synthesis, e.g., a Rink amide resin. The presence of the C-terminal carboxamido group is indicated by the —$NH_2$ group shown on the right hand end of the sequence shown above using standard aminoacid three-letter abbreviations. The Cys-Cys disulfide bridge is shown by the line bridging the $Cys^2$ and $Cys^7$ residues, and the N-terminal "H" indicates a free, unprotected N-terminal amino group.

For an overview of the methods of SITS used herein, see, for example, the following documents, cited in the overview article for "peptide synthesis" at http://en.wikipedia.org/wiki/Peptide_synthesis, as of Aug. 17, 2012:

R. B. Merrifield (1963). "Solid Phase Peptide Synthesis. I. The Synthesis of a Tetrapeptide". *J. Am. Chem. Soc.* 85 (14): 2149-2154.

Mitchell, A. R. K., S. B. H.; Engelhard, M.; Merrifield, R. B. (1978). "A new synthetic route to tert-butyloxycarbonylaminoacyl-4-(oxymethyl)phenylacetamidomethyl-resin, an improved support for solid-phase peptide synthesis". *J. Org. Chem.* 43 (13): 2845-2852.

Wang, S.-S. (1973). "p-alkoxybenzyl alcohol resin and p-alkoxybenzyloxycarbonylhydrazide resin for solid phase synthesis of protected peptide fragments". *J. Am. Chem. Soc* 95 (4): 1328-33. PMID 4687686.

Matsueda, G. R. a. S., J. M. (1981). "A p-methylbenzylhydrlamine resin for improved solid-phase synthesis of peptide amides". *Peptides* 2 (1): 45-50. doi:10.1016/S0196-9781(81)80010-1. PMID 7243625.

Sieber, P. (1987). "A new acid-labile anchor group for the solid-phase synthesis of C-terminal peptide amides by the Fmoc method". *Tetrahedron Lett.* 34: 1269-70.

Schnolzer, M. A., P.; Jones, A.; Alewood, D.; Kent, S. B. H. (2007). "In Situ Neutralization in Boc-chemistry Solid Phase Peptide Synthesis". *Int. J. Peptide Res. Therap.* 13 (1-2): 31-44.

Albericio, F. (2000). *Solid-Phase Synthesis: A Practical Guide* (1 ed.). Boca Raton: CRC Press. p. 848. ISBN 0-8247-0359-6.

Feinberg, R. S.; Merrifield, R. B. (1974). "Zinc chloride-catalyzed chloromethylation of resins for solid phase peptide synthesis". *Tetrahedron* (17): 3209-3212.

Hermkens, P. H. H.; Ottenheijm, H. C. J.; Rees, D. C. (1997). "Solid-phase organic reactions II: A review of the literature November 95-November 96". *Tetrahedron* 53 (16): 5643-5678.

Nilsson B L, Soellner M B, Raines R T (2005). "Chemical Synthesis of Proteins". *Annu. Rev. Biophys. Biamol. Struct.* 34: 91-118. PMC 2845543. PMID 15869385.

Max Bergrnann, Leonidas Zervas (1932). "Über ein allgemeines Verfahren der Peptid-Synthese". *Berichte der deutschen chemischen Gesellschaft* 65 (7): 1192-1201.

K. C. Nicolaou; Natarajan, Swaminathan; Li, Hui; Jain, Nareshkumar F.; Hughes, Robert; Solomon, Michael E.; Ramanjulu, Joshi M.; Boddy, Christopher N. C. et al. (1998). "Total Synthesis of Vancomycin Aglycon—Part 1: Synthesis of Aminoacids 4-7 and Construction of the AB-COD Ring Skeleton". *Angew. Chem. Int. Ed.* 37 (19): 2708-2714.

Schmidt (1998). "Synthetic studies of 14-membered cyclopeptide alkaloids". *Tetrahedron Lett.* 39 (40): 7211-7214.

R. Baker, J. L. Castro (1989). "The total synthesis of (+)-macbecin I". *Chem. Commun.* (6): 378-381.

L. A. Carpino (1993). "1-Hydroxy-7-azabenzotriazole. An efficient peptide coupling additive". *J. Am. Chem. Soc.* 115 (10): 4397-4398.

Zhang, J.-W.; Wu, Cui Rong; Liu, Wen; Zhang, Jing Wen (1991). "Disulfide bond formation in peptides by dimethyl sulfoxide. Scope and applications". *J. Am. Chem. Soc.* 113 (17): 6657-6662.

Sieber, P.; Kamber, B.; Hartmann, A.; Jöhl, Riniker, B.; Rittel, W. (1977). "Total synthesis of human insulin. IV. Description of the final steps (author's transl)", *Helvetica Chimica Acta* 60 (1): 27-37.

Akaji, K.; Fujino, K.; Tatsumi, T.; Kiso, Y. (1993). "Total synthesis of human insulin by regioselective disulfide formation using the silyl chloride-sulfoxide method". *Journal of the American Chemical Society* 115 (24): 11384-11392.

Ottl, J.; Battistuta, R.; Pieper, M.; Tschesche, H.; Bode, W.; Kuhn, K.; Moroder, L. (1996). "Design and synthesis of heterotrimeric collagen peptides with a built-in cystine-knot. Models for collagen catabolism by matrix-metalloproteases". *FEBS Lett* 398 (1): 31-36.

Kapusta, D, R.; Thorkildsen, C; Kenigs, V A; Meier, E; Vinge, M M; Quist, C; Petersen, J S (2005). "Pharmacodynamic Characterization of ZP120 (Ac-RYYRWKKKKKKK-NH2; SEQ ID NO:7), a Novel, Functionally Selective Nociceptin/Orphanin FQ Peptide Receptor Partial Agonist with Sodium-Potassium-Sparing Aquaretic Activity", *Journal of Pharmacology and Experimental Therapeutics* 314 (2): 652-60.

Rizzi A, Rizzi D, Marzola G. et al. (October 2002). "Pharmacological characterization of the novel nociceptin/orphanin FQ receptor ligand, ZP120: in vitro and in vivo studies in mice". *Br. J. Pharmacol.* 137 (3): 369-74, doi: 10.1038/sj.bjp.0704894. PMC 1573505. PMID 12237257.

Stacey A. Palasek, Zachary J. Cox, Jonathan M. Collins (2007). "Limiting racemization and aspartimide formation in microwave-enhanced Fmoc solid phase peptide synthesis". *Journal of Peptide Science* 13 (3): 143-148. doi: 10.1002/psc.804. PMID 17121420.

Atherton, E.; Sheppard, R. C. (1989). *Solid Phase peptide synthesis: a practical approach*. Oxford, England: IRL Press, ISBN 0-19-963067-4.

Stewart, J. M.; Young, J. D. (1984). *Solid phase peptide synthesis* (2nd ed.). Rockford: Pierce Chemical Company. p. 91. ISBN 0-935940-03-0.

The SPPS herein was carried out using N-terminal Fmoc protection, comprising the sequential assembly of aminoacid residue reagents bearing an α-amino protecting group based on 9-fluorenylmethyloxycarbonyl (Fmoc). The Fmoc method allows for a milder deprotection scheme. This method utilizes a base, usually piperidine (20-50%) in DMF in order to remove the Fmoc group to expose the α-amino group for reaction with an incoming activated aminoacid. Fmoc SPPS deprotection uses a base, and thus the exposed amine is neutral.

This allows mild acid-labile protecting groups that are stable under basic conditions, such as Boc and benzyl groups, to be used on the side-chains of aminoacid residues of the target peptide. This orthogonal protecting group strategy is common in organic synthesis. The use of Fmoc-protected N-terminal amino groups in conjunction with tBu and related acid-labile sidechain protection is referred to in the art as the "Fmoc/tBu" type of orthogonal sidechain protection.

As used herein, the designations of "(X)" and "(Y)" in sequences of sidechain-protected, resin-bound peptides (peptide chains) refer to sidechain protecting groups compatible with α-amino Fmoc protecting group chemistry and reaction cycles. As the terms are used herein, an (X) sidechain protecting group is cleaved under acidic conditions (such as the conditions used to free the peptide from the immobilizing resin) to provide a free OH group on an aminoacid sidechain, and (Y) refers to a sidechain protecting group that is cleaved under acidic conditions to provide a free NH or SH group on an aminoacid sidechain. For example, a Tyr(X) residue can be a tyrosine residue with a tert-butyl (tBu) protecting group for the phenolic OH group; a Asn(Y) group can be an asparagine aminoacid residue bearing a trityl (Trt, triphenylmethyl) group on the sidechain carboxamido ((C=O)NH$_2$) moiety. Use of acid-labile sidechain protecting groups with acid-labile resins; i.e., resins that release the synthesized peptides upon treatment with acids such as trifluoroacetic acid (TFA), trifluoromethanesulfonic acid (TFMSA), or even hydrofluoric acid (HF), provides that sidechain protection removal can be accomplished in the same process as cleavage of the final peptide from the immobilizing resin. Accordingly, the (X) and (Y) sidechain protecting groups, examples of which are provided below, can also be labile under conditions of cleavage of the peptide from the solid support (resin), thus including well-known standard sidechain protection as t-butyl, trityl, and the like.

The term "acid labile solid support with substitution value ranging from 0.15-0.60 mmol/g" as used herein refers to a solid support, e.g., an organic polymer or "resin" as the term is used here, comprising one of the insoluble polymers described in the present disclosure wherein the sidechain-protected, resin-bound peptide can be cleaved from the resin by treatment of acid, such as trifluoroacetic acid (TFA), trifluoromethanesulfonic acid (TFMSA), or even hydrofluoric acid (HF). The "substitution value" is the number of millimoles of peptide coupled per gram of resin. Preferably, the substitution value can be about 0.25-0.35 mmole/gm.

The peptide synthesis can be carried out on a resin that provides a C-terminal carboxamido group upon acid cleavage and release of the peptide, such as a Rink amide AM resin. See Hans Rink, *Tet. Lett.* (1987), Volume 28, issue 33, Pages 3787-3790. Along with the development of Fmoc SPPS, different resins have also been created to be removed by TFA. Similar to the Boc strategy, two primary resins are used, based on whether a C-terminal carboxylic acid or amide is desired. As a C-terminal amide is desired, the Rink amide resin is used. Other resins suitable for providing a C-terminal amido group include Rink amide AM resin, 5-(4-N-Fmoc-aminomethyl-3,5dimethoxyphenoxy)valeryl (PAL resin), Nova PEG Rink amide, NovaSyn TG R resin, Rink amide MBHA resin, Rink Amide NovaGel, and Rink amide PEGA resin. The resin is preferably a Rink amide AM resin.

Orthogonal sidechain protection was used, such that sidechain groups are retained throughout the repetitive cycle of SPPS, but are removed, such as under conditions of neat trifluoroacetic acid (TFA) used to detach the peptide chain from the solid support following completion of the synthesis. The following protecting groups were used: Arg(pbf), Asn (trt), Tyr(tBu), Cys(Trt), Lys(Boc), Thr(tBu), Ser(tBu), Gln (Trt), His(Trt). These groups can all be removed from the sidechain-protected resin-bound form of the peptide in the same reaction medium as that in which cleavage is carried out.

The repetitive synthesis procedures for C-terminal to N-terminal SPPS are well known in the art, comprising anchoring the N-terminal aminoacid (AA) residue to the resin), Fmoc group removal for N-terminal amino group liberation, then sequential coupling and Fmoc removal of each subsequent desired residue, suitably sidechain-protected as necessary, until the final sidechain-protected, resin-bound peptide is obtained. Then, removal from the resin and sidechain deprotection is carried out, e.g., using trifluoroacetic acid to cleave the peptide from the resin and to remove acid-labile sidechain protection.

In development of the invention route, after several unsuccessful experiments using different strategies varying loading substitution rates of the resin and use of modified coupling agents like HBTU/NMM for synthesizing the 37 mer amyloid analog in single sequential procedure for the entire 37-mer on a solid support, even by using molar excesses of Fmoc protected aminoacids, the synthesis of the target never achieved completion. In WO2009003666 the use of three pseudoproline moieties for the synthesis of full length human amylin 1-37 was described, which adds to the cost of synthesis.

However, the applicants herein have surprisingly found that by just insertion of a single pseudoproline moeity, the target crude peptide was synthesized with a remarkable purity of ≥30%. Another surprising finding was by just adding 0.1M HOBt to the deprotection solvent, the purity of the crude peptide increased to ≥35%. An embodiment of the present invention is the use of a single pseudoproline moiety for the synthesis of the 37-mer peptide, Pramlintide, in good yield and purity, but without the added expense of using more than a single equivalent of a pseudoproline-type protected aminoacid residue in the entire 37-mer synthetic procedure.

Following cleavage of the peptide of formula (4) from the resin, concomitant with sidechain deprotection, the product can be purified by reverse phase HPLC(RP-HPLC), then oxidized, or the product can be oxidized, and the peptide of formula (1) purified by RP-HPLC, or both peptides can be purified in this manner.

In various embodiments, the invention provides a process for the production of pramlintide, a disulfide-bridged peptide of formula (1):

(formula 1; SEQ ID NO: 1)

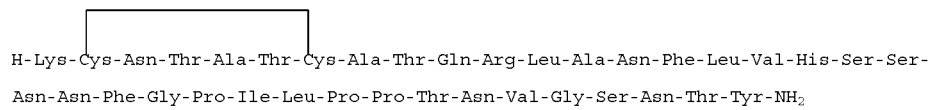

H-Lys-Cys-Asn-Thr-Ala-Thr-Cys-Ala-Thr-Gln-Arg-Leu-Ala-Asn-Phe-Leu-Val-His-Ser-Ser-Asn-Asn-Phe-Gly-Pro-Ile-Leu-Pro-Pro-Thr-Asn-Val-Gly-Ser-Asn-Thr-Tyr-NH$_2$ wherein the Cys-Cys line indicates a cystine disulfide bridge;

comprising:

(a) coupling Fmoc-Tyr(X)-OH to an acid-labile resin with a substitution value ranging from 0.15-0.60 mmol/g, to provide a sidechain-protected resin-bound tyrosine residue, Fmoc-Tyr(X)-Resin; then, (b) removing the N-terminal Fmoc protecting group thereof using piperidine in 1-hydroxybenzotriazole (HOBt) in polar aprotic solvent to provide an N-terminal free amino group; then, (c) assembling each respective Fmoc-protected aminoacid residue sequentially C-terminal to N-terminal under conditions suitable for peptide coupling, to provide sidechain-protected resin-bound peptide of the formula (2RBP):

Fmoc-Asn(Y)-Asn(Y)-Phe-Gly-Pro-Ile-Leu-Pro-Pro-Thr(X)-Asn(Y)-Val-Gly-Ser(X)-Asn(Y)-Thr(X)-Tyr(X)-Resin (SEQ ID NO:2);

wherein (X) and (Y) signify acid-labile sidechain protecting groups, wherein (X) can be removed under acidic conditions to yield a free OH group and (Y) can be removed under acidic conditions to yield a free NH or SH group; then, (d) removing the N-terminal Fmoc group using piperidine in 1-hydroxybenzotriazole (HOBt) in polar aprotic solvent to provide an N-terminal free amino group; then, (e) coupling Fmoc-Ser(X)-Ser($\Psi^{Me,Me}$ Pro)-OH to the N-terminal free amino group, under conditions suitable for peptide coupling, wherein Ser($\Psi^{Me,Me}$ Pro) signifies a pseudoproline serine-derived oxazolidine of formula

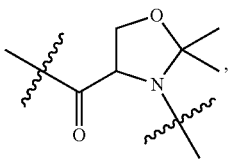 [SMILES: *C(=O)C1COC(C)(C)N1*]

wherein each wavy line indicates a point of bonding in the peptide chain, to yield a sidechain-protected resin-bound peptide of Formula (3RBP):

Fmoc-Ser(X)-Ser($\Psi^{Me,Me}$ Pro)-Asn(Y)-Asn(Y)-Phe-Gly-Pro-Ile-Leu-Pro-Pro-Thr(X)-Asn(Y)-Val-Gly-Ser(X)-Asn(Y)-Thr(X)-Tyr(X)-Resin (SEQ ID NO:3); then, (f) further assembling each respective Fmoc-protected aminoacid residue sequentially C-terminal to N-terminal, under conditions suitable for stepwise N-terminal Fmoc removal and peptide coupling, to the sidechain-protected resin-bound peptide of formula (3RBP), to provide a sidechain-protected resin-bound peptide of formula (4RBP):

Fmoc-Lys(Boc)-Cys(Y)-Asn(Y)-Thr(X)-Ala-Thr(X)-Cys(Y)-Ala-Thr(X)-Gln(Y)-Arg(Pbf)-Leu-Ala-Asn(Y)-Phe-Leu-Val-His(Y)-Ser(X)-Ser($\Psi^{Me,Me}$ Pro)-Asn(Y)-Asn(Y)-Phe-Gly-Pro-Ile-Leu-Pro-Pro-Thr(X)-Asn(Y)-Val-Gly-Ser(X)-Asn(Y)-Thr(X)-Tyr(X)-Resin (SEQ ID NO:4);

with a purity of crude peptide of >30%; then, (g) sidechain-deprotecting and cleaving a 37-mer cysteine-reduced peptide of Formula (4) from the resin by contacting with acid,
H-Lys-Cys-Asn-Thr-Ala-Thr-Cys-Ala-Thr-Gln-Arg-Leu-Ala-Asn-Phe-Leu-Val-His-Ser-Ser-Asn-Asn-Phe-Gly-Pro-Ile-Leu-Pro-Pro-Thr-Asn-Val-Gly-Ser-Asn-Thr-Tyr-NH$_2$ (formula (4); SEQ ID NO:5); then, (h) oxidizing the peptide of formula (4) to the disulfide-bridged peptide of Formula (1), and, (i) purifying the peptide of formula (4), or the peptide of formula (1), or optionally both, by RP-HPLC.

For example, the acid-labile resin can be selected from the group consisting of Rink amide AM resin, 5-(4-N-Fmoc-aminomethyl-3,5-dimethoxyphenoxy)valeryl-(PAL resin), Nova PEG-Rink amide, Nova Syn TG R resin, Rink amide MBHA resin, Rink Amide NovaGel, and Rink amide PEGA resin. More specifically, the resin can be Rink amide AM resin. More specifically, the acid-labile resin can have a substitution value ranging from 0.25 to 0.35 mmole/gm.

The Ser($\Psi^{Me,Me}$ Pro) aminoacid residue is of formula

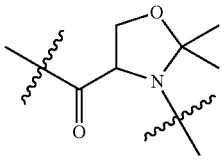 [SMILES: *C(=O)C1COC(C)(C)N1*]

the $\Psi^{Me,Me}$ Pro designation indicating that the pseudoproline form of sidechain-protected serine is the 2,2-dimethyloxazolidine, wherein the wavy lines indicate to points of bonding of the protected serine residue in the growing resin-bound peptide chain. As is apparent, the 2,2-dimethyloxazolidine results from reaction of the ketone acetone with the serine to yield the heterocyclic aminal. Upon acid cleavage, such as under the conditions for release from the resin, the aminal is hydrolyzed back to the free hydroxymethyl sidechain of serine, with the nitrogen atom and carbonyl groups incorporated into the peptide chain.

When the peptide is released from the resin and the sidechain protection removed, the two cysteine residues are in their thiol, or reduced form. This is referred to as the linear form of the 37-mer peptide of formula (4). Upon oxidation resulting in disulfide bond formation between the two thiol groups, the peptide of formula (1) is obtained. This is referred to as the cyclic, or oxidized, form of the 37-mer peptide. It is this form, e.g., as its acetate salt, that is used therapeutically, e.g., in the treatment of diabetes, and is termed pramlintide, having the trade name of Symlin®, produced by Amylin Pharmaceuticals, Inc.

Either the reduced (thiol) peptide, of formula (4), or the oxidized (disulfide) peptide, of formula (1), or both, can be purified by RP-HPLC to provide a product of good purity. The acetate salt of the peptide of formula (1), pramlintide, can be obtained in sufficient purity for pharmaceutical use.

In various embodiments, the polar aprotic solvent used is dimethyl formamide (DMF).

In various embodiments, the (X) group can be selected from the group consisting of tBu, Trt, and chlorotrityl, and the (Y) group can be selected from the group consisting of Trt, Tmob, Mtt, and Xan. More specifically, the (X) group can be tBu. More specifically, the (Y) group can be Trt. The abbreviations, well-known to those of skill in the art, are defined in more detail below.

In various embodiments, Fmoc removal at each sequential step of assembly can be carried out in a medium comprising 0.1M-0.5M-hydroxybenzotriazole (HOBt) in 20%-50% piperidine in DMF. It has been unexpectedly discovered by the inventors herein that the purity of the final peptide is increased when carrying out the Fmoc removal step in a medium including the HOBt, compared to use of comparable conditions wherein the HOBt is absent.

After the step of sidechain deprotection and cleavage of the final peptide of formula (4) from the resin, conversion to the peptide of formula (1) comprising the cystine disulfide bridge can be carried out by a step wherein the peptide of Formula (4) is subjected to air oxidation, or hydrogen peroxide or copper sulphate or iodine oxidation, to yield cyclic peptide of Formula (1).

In various embodiments, the invention provides peptide of formula (1) prepared by an inventive process as disclosed and claimed herein. For example, the peptide can be in the form of an acetate salt, pramlintide, for medicinal use. Accordingly, the invention provides a pharmaceutical composition comprising the peptide of formula (1), e.g., as the acetate salt, and a pharmaceutically acceptable excipient.

In various embodiments, the invention provides a sidechain-protected resin-bound peptide of Formula (4RBP):
Fmoc-Lys(Boc)-Cys(Y)-Asn(Y)-Thr(X)-Ala-Thr(X)-Cys(Y)-Ala-Thr(X)-Gln(Y)-Arg(Pbf)-Leu-Ala-Asn(Y)-Phe-Leu-Val-His(Y)-Ser(X)-Ser($\Psi^{Me,Me}$Pro)-Asn(Y)-Asn(Y)-Phe-Gly-Pro-Ile-Leu-Pro-Pro-Thr(X)-Asn(Y)-Val-Gly-Ser(X)-Asn(Y)-Thr(X)-Tyr(X)-Resin (SEQ ID NO:4); wherein (X), (Y), Ser($\Psi^{Me,Me}$ Pro), and Resin are as described herein. For example, the Resin can be a Rink resin.

For example, the invention provides a sidechain-protected resin-bound peptide of Formula (5RBP):
Fmoc-Lys(Boc)-Cys(Trt)-Asn(Trt)-Thr(tBu)-Ala-Thr(tBu)-Cys(Trt)-Ala-Thr(tBu)-Gln(Trt)-Arg(Pbf)-Leu-Ala-Asn(Trt)-Phe-Leu-Val-His(Trt)-Ser(tBu)-Ser($\Psi^{Me,Me}$Pro)-Asn(tBu)-Asn(Trt)-Phe-Gly-Pro-Ile-Leu-Pro-Pro-Thr(tBu)-Asn(Trt)-Val-Gly-Ser(tBu)-Asn(Trt)-Thr(tBu)-Tyr(tBu)-Resin (SEQ ID NO:6) wherein Ser($\Psi^{Me,Me}$ Pro) and Resin are as described herein. For example, the Resin can be a Rink resin.

In other embodiments, the invention provides a sidechain-protected resin-bound peptide fragment of Formula (3RBP):

Fmoc-Ser(X)-Ser($\Psi^{Me,Me}$ Pro)-Asn(Y)-Asn(Y)-Phe-Gly-Pro-Ile-Leu-Pro-Pro-Thr(X)-Asn(Y)-Val-Gly-Ser(X)-Asn(Y)-Thr(X)-Tyr(X)-Resin (SEQ ID NO:3); wherein (X), (Y), Ser($\Psi^{Me,Me}$ Pro), and Resin are as described herein. For example, the Resin can be a Rink resin.

For example, the invention provides a sidechain-protected resin-bound peptide fragment of Formula (3RBP) is Fmoc-Ser(tBu)-Ser($\Psi^{Me,Me}$Pro)-Asn(tBu)-Asn(Trt)-Phe-Gly-Pro-Ile-Leu-Pro-Pro-Thr(tBu)-Asn(Trt)-Val-Gly-Ser(tBu)-Asn(Trt)-Thr(tBu)-Tyr(tBu)-Resin (SEQ ID NO:8), wherein Ser ($\Psi^{Me,Me}$ Pro) and Resin are as defined herein.

Ser($\Psi^{Me,Me}$ Pro) signifies a pseudoproline serine-derived oxazolidine of formula

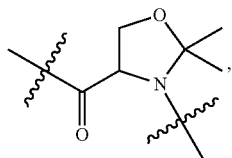

wherein each wavy line indicates a point of bonding.

In various embodiments, the invention provides a method of treatment of diabetes, comprising administering to a patient in need thereof a peptide of formula (1), pramlintide, or an pharmaceutically acceptable salt thereof, e.g., an acetate salt, or a pharmaceutical composition comprising a peptide of formula (1) or a pharmaceutically acceptable salt thereof, e.g., an acetate salt, in a composition further comprising a pharmaceutically acceptable excipient, suitable for subcutaneous administration of the pramlintide. Pramlintide acetate is typically administered as an injection by diabetes patients, and is known by the trade name Symlin®.

In various embodiments, the method of treatment further comprises administration of an effective amount of a second anti-diabetic drug.

In various embodiments, the invention further provides a kit, comprising an effective amount of a peptide or a pharmaceutical composition prepared by a method of the invention, optionally disposed as an isotonic solution, optionally as the acetate salt thereof, in a syringe for subcutaneous administration; the kit optionally further comprising instructional material.

Additional advantages of the invention will be set forth by the description which follows, and in part will be obvious from the description, or may be learnt by the practice of the invention. The advantages of the invention may be realised and attained by means of the elements and combinations particularly pointed out in the appended claims. It is to be understood that the foregoing general description and the following detailed description are exemplary and explanatory only and are not restrictive of the invention, as claimed.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

EXAMPLES

Abbreviations Used:
Acm: acetamidomethyl
ACN: acetonitrile
Al: allyl
Ala: alanine
Aloc: allyloxycarbonyl
Arg: arginine
Asn: asparagine
Asp: aspartic acid.
Boc: t-butyloxycarbonyl
CTC resin: Chlorotrityl resin
Cys: cysteine
DCM: dichloromethane
DIC: Diisopropylcarbodiimide
DIPEA: Diisopropylethylamine
DMF: N,N-dimethylformamide
DMSO: Dimethyl Sulfoxide
DTT: dithiothreitol
EDT: 1,2-ethanedithiol
EDTA: Ethylenediamine tetraceticacid.
Fmoc: 9-fluorenylmethoxycarbonyl
Gln: glutamine
Glu: glutamic acid
Gly: glycine
HATU: 2-(1H-7-azabenzotriazol-1-yl)-1,1,3-tetramethyluronium hexafluorophosphate methanaminium
His: histidine
Hmb: (2-hydroxy-4-methoxybenzyl)
HOBt: N-hydroxy benzotriazole
HPLC: high performance liquid chromatography
Ile: isoleucine
Leu: leucine
Lys: lysine
Mbh: 4,4-dimethyloxybenzhydryl
MBHA resin: Methylbenzylhydrylamine resin
MeOH: methanol
Met: methionine
Mtr: methoxytrimethylbenzene sulfonyl
Mtt: 4-methyltrityl
NMP: N-methylpyrrolidone
OAl: allyl ester
Orn: ornithine
OtBu: t-butyl ester
Pbf: 2,2,4,6,7-pentamethyl-dihydrobenzofuran-5-sulfonyl
pGlu: pyroglutamic acid or pyrrolidone glutamic acid
Phe: phenylalanine
Pmc: 2,2,5,7,8-pentamethyl-chroman-6-sulfonyl chloride
Pro: proline
SDS: sodium dodecyl sulfate
Ser: serine
tBu: t-butyl
TCTU: O-(6-Chloro-1-hydrocibenzotriazol-1-yl)-1,1,3-tetramethyluronium tetrafluoroborate
TES: triethylsilane
TFA: trifluoroacetic acid
Thr: threonine
TIPS, TIS: triisopropylsilane
Tmob: 2,4,6-trimethoxybenzyl, Trp: tryptophan
Trt: trityl or triphenylmethyl
Tyr: tyrosine
Val: valine
Xan: xanthyl
Z: Benzyloxycarbonyl
6-Cl HOBt: 6-Chloro-1-Hydroxy-1H-Benzotriazole
Synthesis of Linear Precursors on Solid Support Using Pseudoproline ($^{19}$Fmoc-Ser(tBu)-$^{20}$Ser($\Psi^{Me,Me}$pro)-OH):

Fmoc-Rink amide AM resin with a low substitution value ranging from 0.28-33 mmole/gram (about 8.3 gm resin, 2.5 mmole) was swelled in DMF for 1 hr by agitation under nitrogen. The Fmoc protecting group was removed by treating with 20% piperidine in DMF, followed by the through washing of the resin with DMF. The coupling of the first aminoacid Fmoc-Tyr(tBu)-OH (6.25-8.75 mmole, 2.5-3.5 eq)), was carried out by addition of HBTU (6.25-8.75 mmole, 2.5-3.5 eq) and NMM (0.4M in DMF). The mixture was stirred for 1 hr. The completion of coupling reaction, was confirmed by the ninhydrin test after washing of the resin. The subsequent removal of the Fmoc protecting group was removed with 20% piperidine in DMF/20% piperidine in 0.1M HOBt in DMF in all the aminoacid deprotections. The resin was thoroughly washed with DMF before the addition of the next aminoacid. These steps were repeated each time with the successive aminoacid according to the peptide sequence. The trifunctional aminoacid were side chain protected as follows: Arg(pbf), Asn(trt), Tyr(tBu), Cys(Trt), Lys (Boc), Thr(tBu), Ser(tBu), Gln(Trt), His(Trt). Post completion of the synthesis, the resin was thoroughly washed with DMF and DCM. The pseudoproline dipeptide, Fmoc-Ser (tBu)-Ser($\Psi^{Me,Me}$, pro)-OH) was incorporated using the standard synthesis cycle using 2.5× excess only. Additionally pseudoproline dipeptide, Fmoc-Thr(tBu)-Asn($\Psi^{Me,Me}$, pro)-OH) was incorporated using the standard synthesis cycle using 2.5× excess only at position 3 and 4 of the 37mer peptide.

Weight of the peptidyl resin: 22-25 gm

Cleavage of Linear Precursors on Solid Support:

The cleavage of the peptide from the resin with simultaneous deprotection of all the protecting groups was carried out by the treatment of either of the cocktail cleavage mixtures stated below:
1. TFA:TIS:Water (95:2.5:2.5 v/v)
2. TFA:TIS:DTT:Water (94:01:2.5:2.5 v/v; w/v)
3. TFA:TIS:Phenol:DTT:Water (82.5:05:0.5:2.5:05 v/v; w/v)
4. TFA:DTT:Thioanisol:Phenol:Water (82.5:2.5:05:05:05 v/v; w/v)
5. TFA:EDT:Thioanisol:Phenol:Water (82.5:2.5:05:05:05 v/v)
6. TFA:TIS:Water:EDT (94:01:2.5:2.5 v/v)

The cleavage was carried out at 2-8° C. for 20 minutes followed by then stirring the peptidyl resin for 2.5 hours at ambient temperature. The crude cleavage mixture was then filtered, the resin washed thoroughly with TFA. The crude cleavage peptide solution was concentrated on a rotary evaporator. The precipitation was effected using cold diisopropyl ether (DIPE) and stored at −20° C. overnight. The peptide precipitate was filtered and dried under vacuum for 16 hrs. The preferred cleavage mixture was the K reagent replacing EDT with DTT of them all.

The isolated yield of the crude peptide: 6-8 g.

Synthesis of Linear Precursors on Solid Support Using Low Loading Fmoc-Rink Amide AM Resin (9.28-0.333 mmol/g):

Fmoc-Rink amide AM resin with a low substitution value ranging from 0.28-0.33 mmole/gram (about 8.3 gm resin, 2.5 mmole) was swelled in DMF for 1 hr by agitation under nitrogen. The Fmoc protecting group was removed by treating with 20% piperidine in DMF, followed by the through washing of the resin with DMF. The coupling of the first aminoacid Fmoc-Tyr(tBu)-OH (6.25-8.75 mmole, 2.5-3.5 eq)), was carried out by addition of HBTU (6.25-8.75 mmole, 2.5-3.5 eq)) and NMM (0.4M in DMF). The mixture was stirred for 1 hr. The completion of coupling reaction, was confirmed by the ninhydrine test after washing of the resin.

Figure 2:
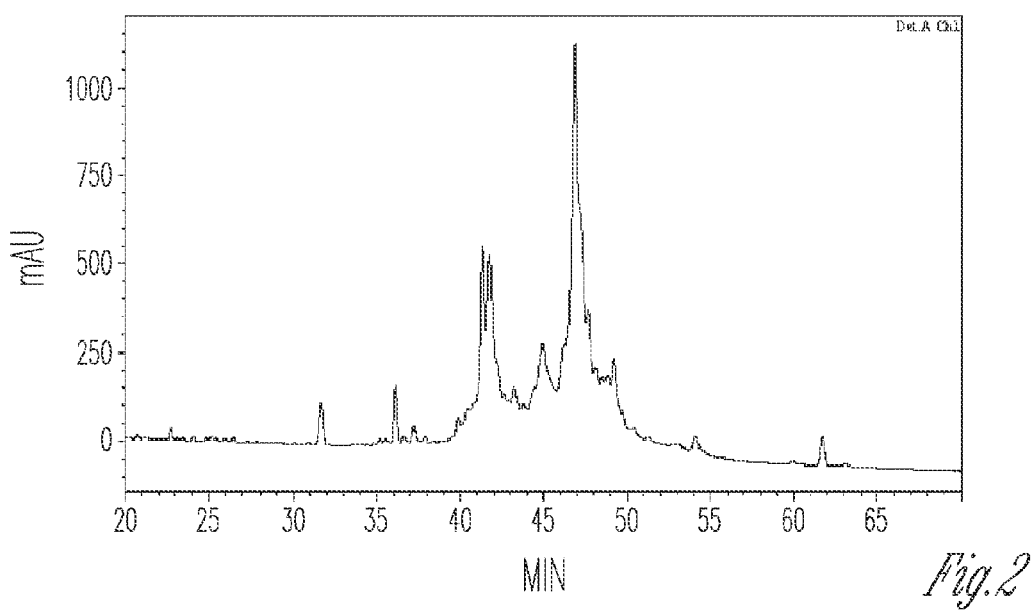
FIG. 2 is an RP-HPLC chromatogram of crude cleavage mixture of Pramlintide (linear reduced form) synthesized using low loading Fmoc-Rink amide AM resin.

The subsequent removal of the Fmoc protecting group was removed with 20% piperidine in DMF in all the aminoacid deprotections. The resin was thoroughly washed with DMF before the addition of the next aminoacid. These steps were repeated each time with the successive aminoacid according to the peptide sequence. The trifunctional aminoacid were side chain protected as follows: Arg(pbf), Asn(trt), Glu (OtBu), Tyr(tBu), Cys(Trt), Lys(Boc), Thr(tBu), Ser(tBu), Gln(Trt), His(Trt). Post completion of the synthesis, the resin was thoroughly washed with DMF and DCM. The crude purity of the product was highly inconsistent and in some of the batches the product was not formed or was of unacceptable quality (FIG. 2).

Similarly synthesis of pramlintide was carried out using standard loading range of 0.50-0.60 mmole/g. Performing the synthesis using this strategy, the crude purity of the product was highly inconsistent and in some of the batches the product was not formed or was of unacceptable quality (FIG. 1).

Cleavage of Linear Precursors on Solid Support:

The cleavage of the peptide from the resin with simultaneous deprotection of all the protecting groups was carried out by the treatment of either of the cocktail cleavage mixtures stated below:
1. TFA:TIS:Water(95:2.5:2.5 v/v)
2. TFA:TIS:DTT:Water(94:01:2.5:2.5 v/v; w/v)
3. TFA:TIS:Phenol:DTT:Water (82.5:05:0.5:2.5:05 v/v; w/v)
4. TFA:DTT:Thioanisol:Phenol:Water (82.5:2.5:05:05:05 v/v; w/v)
5. TFA:EDT:Thioanisol:Phenol:Water (82.5:2.5:05:05:05 v/v)
6. TFA:TIS:Water:EDT (94:01:2.5:2.5 v/v)

The cleavage was carried out at 2-8° C. for 20 minutes followed by then stirring the peptidyl resin for 2.5 hours at ambient temperature. The crude cleavage mixture was then filtered, the resin washed thoroughly with TFA. The crude cleavage peptide solution was concentrated on a rotary evaporator. The precipitation was effected using cold diisopropyl ether (DIPE) and stored at −20° C. overnight. The peptide precipitate was filtered and dried under vacuum for 16 hrs. The preferred cleavage mixture was the K reagent replacing EDT with DTT of them all.

Figure 3:
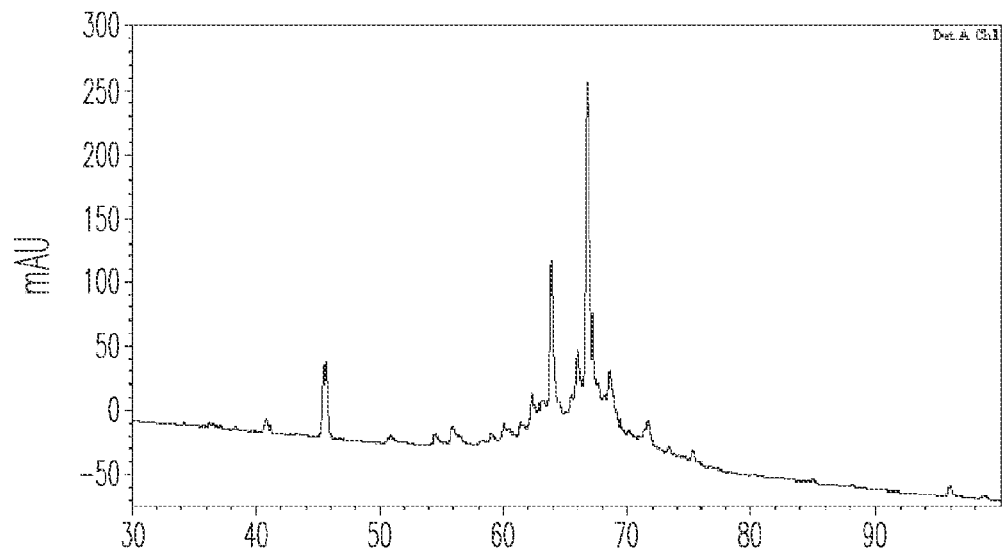
FIG. 3 is an RP-HPLC chromatogram of crude cleavage mixture of Pramlintide (linear reduced form) (RP-HPLC purity 25%) synthesized using low loading Fmoc-Rink amide AM resin and single pseudoproline (Ser-Ser)19-20.
Figure 4:
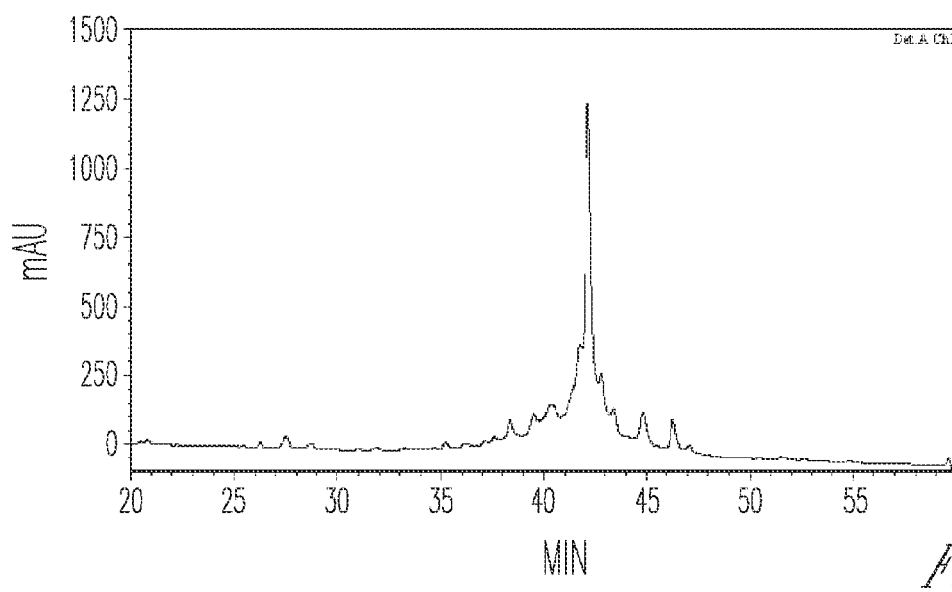
FIG. 4 is an RP-HPLC chromatogram of crude cleavage mixture of Pramlintide (linear reduced form) (RP-HPLC purity 30%) synthesized using low loading Fmoc-Rink amide AM resin and using pseudoprolines (dipeptides) at two positions (Ser-Ser)19-20 and (Thr-Asn) 3-4.
Figure 5:
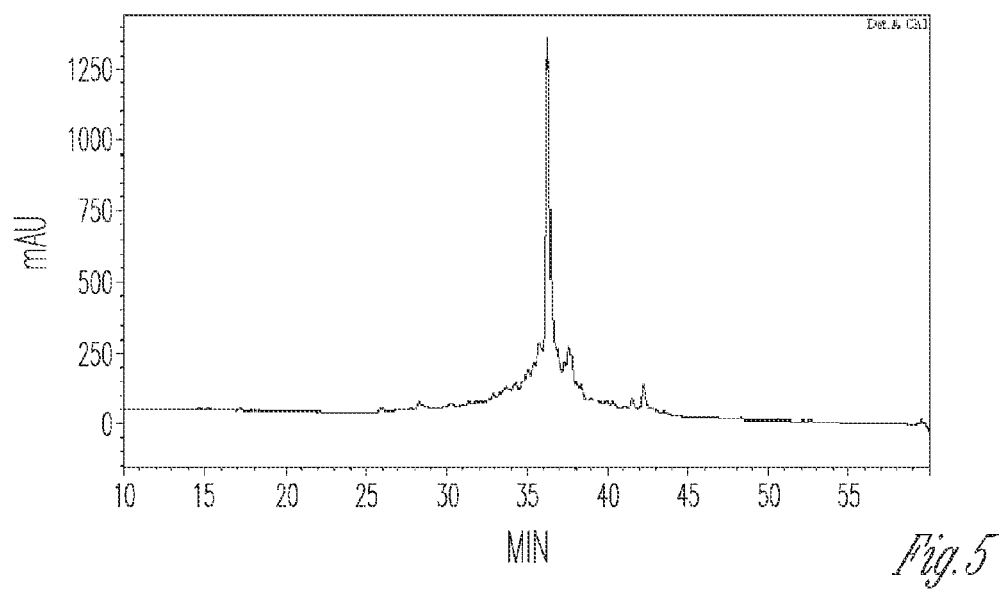
FIG. 5 is an RP-HPLC chromatogram of crude cleavage mixture of Pramlintide (linear reduced form), (RP-HPLC purity 37%) synthesized using low loading Fmoc-Rink amide AM resin, using pseudoproline-(Ser-Ser)19-20 and using 0.1M HOBt-piperidine-DMF combination.
Figure 6:
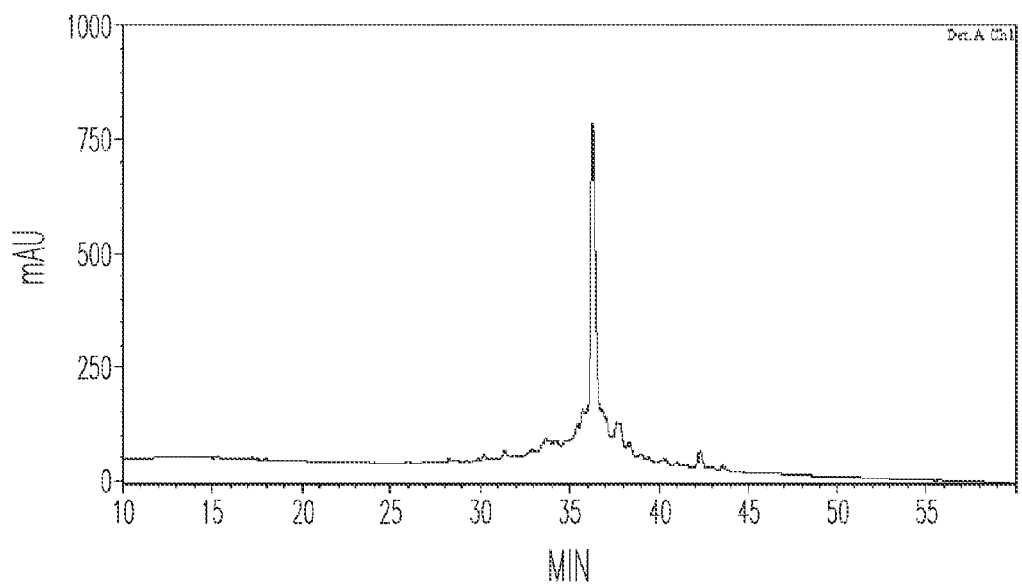
FIG. 6 is an RP-HPLC chromatogram of crude cleavage mixture of Pramlintide (linear reduced form), (RP-HPLC purity 39%) synthesized using low loading Fmoc-Rink amide AM resin, using pseudoprolines at two positions (Ser-Ser)19-20 and (Thr-Asn)3-4 and using 0.1M HOBt-piperidine-DMF combination.

The crude purity of the product using 20% piperidine in DMF and single pseudoproline was determined by HPLC (FIG. 3). The crude purity of the product using 20% piperidine in DMF and two pseudoprolines was determined by HPLC (FIG. 4). The crude purity of the product using 20% piperidine in 0.1M HOBt in DMF and single pseudoproline was determined by HPLC (FIG. 5). The crude purity of the product using 20% piperidine in 0.1M HOBt in DMF and two pseudoprolines was determined by HPLC (FIG. 6).

Purification of the Linear Peptide:

The crude linear (reduced) peptide was taken up for purification by RP-HPLC. Post purification the fractions were analyzed for the purity. The fraction containing purity in the range of 75-85% were pooled and lyophilized and were further taken up for the oxidation or were taken in the solution form itself.

Oxidation of the Linear Peptide:
a) Using Hydrogen Peroxide Oxidation Method:

The peptide was dissolved in 20% acetic acid at concentration of 0.1-1.0 mg/ml, followed by the addition of aqueous ammonia solution (28%) to adjust the pH to about 8.5. Calculated fixed amount of Hydrogen peroxide solution was added at regular intervals. After the addition of peroxide ceased, the reaction mixture was stirred for about 1 hr-2 hrs. The reaction was quenched by lowering the pH to 3.0 by using 20% acetic acid. The reaction mixture was then taken up for the RP-HPLC analysis & further purified b) Using Copper Sulfate Oxidation Method The peptide was dissolved in 25% acetonitrile in 0.1% TFA at concentration of 1.0-2.0 mg/ml, followed by the addition of ammonium hydroxide solution to adjust the pH to about 8.5. Calculated amount of copper sulfate (solid or in water) was added. The reaction mixture was stirred overnight, till the completion of oxidation, as monitored by RP-HPLC. The reaction was quenched by towering the pH to 4.0 by using 20% acetic acid. The reaction mixture was then taken up for the RP-HPLC analysis & further purified Alternatively the oxidation reactions can also be carried out by using standard reagents like Iodine-methanol, Iodine-acetic acid, or air oxidation using the optimized conditions.

Purification of the Cyclic Peptide & Salt Exchange:

The cyclic peptide was taken up for purification by RP-HPLC. Post purification, the fractions were analyzed for the purity. The fraction containing >97% were pooled and lyophilized and were further taken up for salt exchange. The salt exchange was performed only RP-HPLC using acetate buffer or ammonium acetate. The fractions were pooled and were lyophilized and stored at −20° C.

The salt exchange was carried out by using ion exchange chromatography. Medias such as Dowex ion exchange resins could also be used for the salt exchange.

Figure 7:
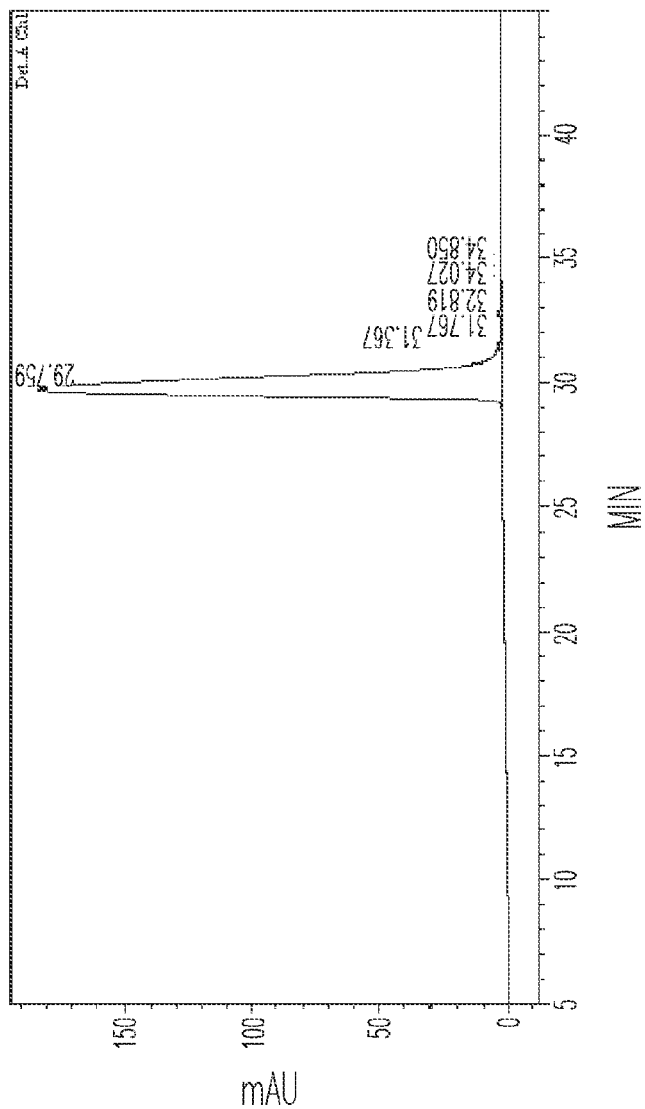
FIG. 7: RP-HPLC chromatogram of purified Pramlintide acetate (RP-HPLC purity 98.79%)
Figure 8:
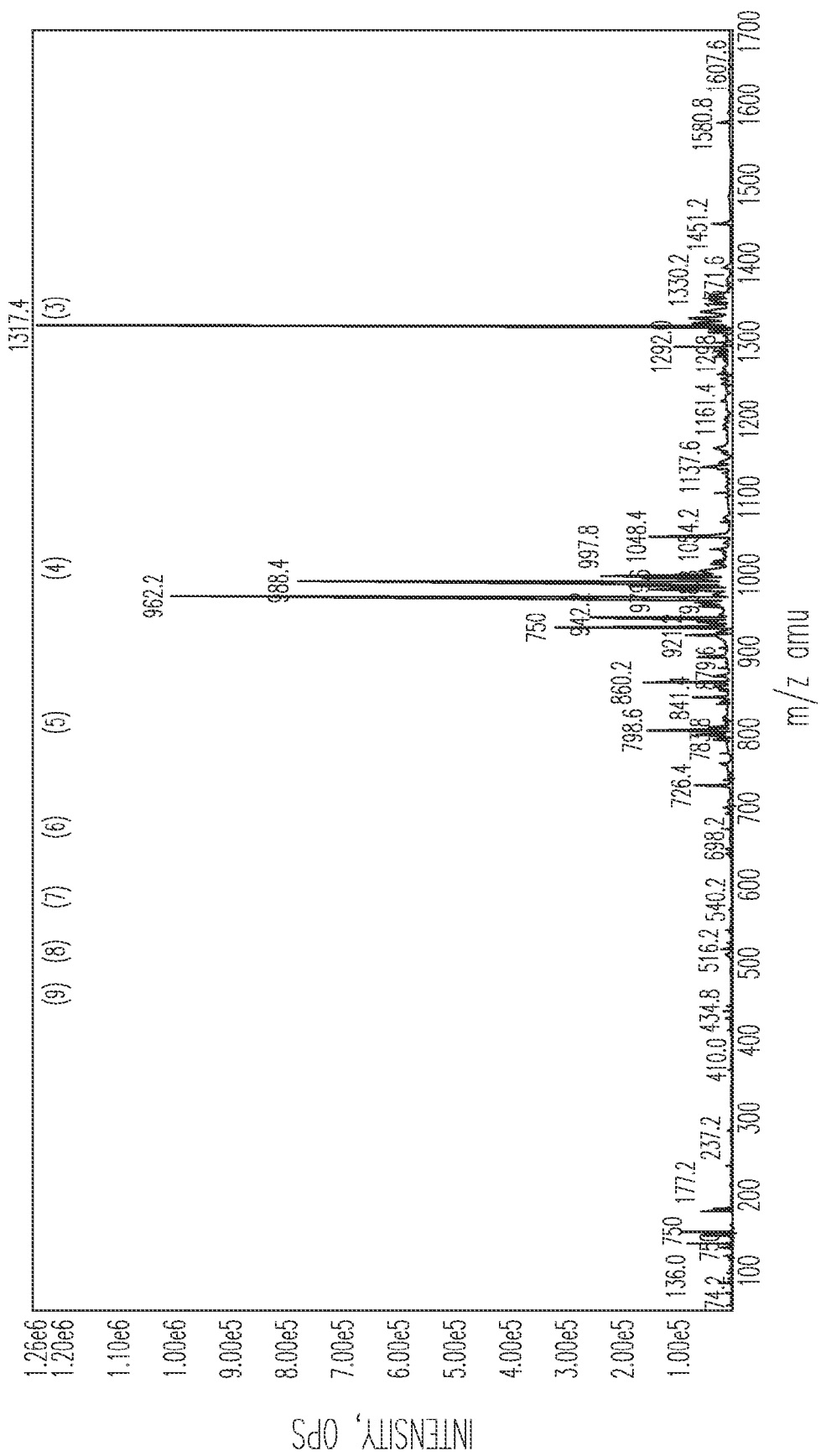
FIG. 8: ESI-MS of Pramlintide acetate: Expected mass 3949 Da; Mass Found: 3949.2 Da

The overall isolated purification yield was 5-10%. HPLC chromatogram of purified pramlintide acetate is depicted in FIG. 7 and mass is depicted in FIG. 8.

---

What is claimed is:

1. A process for the production of pramlintide, a disulfide-bridged peptide of formula (1):

(formula 1; SEQ ID NO: 1)

H-Lys-Cys-Asn-Thr-Ala-Thr-Cys-Ala-Thr-Gln-Arg-Leu-
Ala-Asn-Phe-Leu-Val-His-Ser-Ser-Asn-Asn-Phe-Gly-
Pro-Ile-Leu-Pro-Pro-Thr-Asn-Val-Gly-Ser-Asn-Thr-
Tyr-NH$_2$, wherein the Cys-Cys line indicates a cystine disulfide bridge;
comprising:
(a) coupling Fmoc-Tyr(X)-OH to an acid-labile Rink amide AM resin with a substitution value ranging from 0.15-0.60 mmol/g, in a single coupling reaction, to provide a sidechain-protected resin-bound tyrosine residue, Fmoc-Tyr(X)-Resin; then,
(b) removing the N-terminal Fmoc protecting group thereof using piperidine in 1-hydroxybenzotriazole (HOBt) in polar aprotic solvent to provide an N-terminal free amino group; then,
(c) assembling each respective Fmoc-protected aminoacid residue sequentially C-terminal to N-terminal under conditions suitable for peptide coupling, to provide sidechain-protected resin-bound peptide of the formula (2RBP):

Fmoc-Asn(Y)-Asn(Y)-Phe-Gly-Pro-Ile-Leu-Pro-Pro-Thr(X)-Asn(Y)-Val-Gly-Ser(X)-Asn(Y)-Thr(X)-Tyr(X)-Resin (SEQ ID NO:2);
wherein (X) and (Y) signify acid-labile sidechain protecting groups, wherein (X) can be removed under acidic conditions to yield a free OH group and (Y) can be removed under acidic conditions to yield a free NH or SH group; then,
(d) removing the N-terminal Fmoc group using piperidine in 1-hydroxybenzotriazole (HOBt) in polar aprotic solvent to provide an N-terminal free amino group; then,
(e) coupling Fmoc-Ser(X)-Ser($\Psi^{Me,Me}$ Pro)-OH to the N-terminal free amino group, under conditions suitable for peptide coupling, wherein Ser($\Psi^{Me,Me}$ Pro) signifies a pseudoproline serine-derived oxazolidine of formula

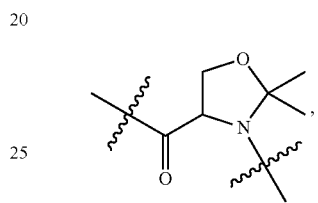

wherein each wavy line indicates a point of bonding in the peptide chain, to yield a sidechain-protected resin-bound peptide of Formula (3RBP):

Fmoc-Ser(X)-Ser($\Psi^{Me,Me}$ Pro)-Asn(Y)-Asn(Y)-Phe-Gly-Pro-Ile-Leu-Pro-Pro-Thr(X)-Asn(Y)-Val-Gly-Ser(X)-Asn(Y)-Thr(X)-Tyr(X)-Resin (SEQ ID NO:3); then, (f) further assembling each respective Fmoc-protected aminoacid residue sequentially C-terminal to N-terminal, under conditions suitable for stepwise N-terminal Fmoc removal and peptide coupling, to the sidechain-protected resin-bound peptide of formula (3RBP), to provide a sidechain-protected resin-bound peptide of formula (4RBP), wherein the Ser($\Psi^{Me,Me}$Pro is the sole pseudoproline serine-derived oxazolidine in the peptide of formula (4RBP):

Fmoc-Lys(Boc)-Cys(Y)-Asn(Y)-Thr(X)-Ala-Thr(X)-Cys(Y)-Ala-Thr(X)-Gln(Y)-Arg(Pbf)-Leu-Ala-Asn(Y)-Phe-Leu-Val-His(Y)-Ser(X)-Ser($\Psi^{Me,Me}$ Pro)-Asn(Y)-Asn(Y)-Phe-Gly-Pro-Ile-Leu-Pro-Pro-Thr(X)-Asn(Y)-Val-Gly-Ser(X)-Asn(Y)-Thr(X)-Tyr(X)-Resin (SEQ ID NO:4);
with a purity of crude peptide of ≥30%; then,
(g) sidechain-deprotecting and cleaving a 37-mer cysteine-reduced peptide of Formula (4) from the resin by contacting with acid, H-Lys-Cys-Asn-Thr-Ala-Thr-Cys-Ala-Thr-Gln-Arg-Leu-
Ala-Asn-Phe-Leu-Val-His-Ser-Ser-Asn-Asn-Phe-Gly-Pro-
Ile-Leu-Pro-Pro-Thr-Asn-Val-Gly-Ser-Asn-Thr-Tyr-NH$_2$
(formula (4); SEQ ID NO:5); then,
(h) oxidizing the peptide of formula (4) to the disulfide-bridged peptide of Formula (1) by air oxidation, or hydrogen peroxide or copper sulphate or iodine oxidation; and,
(i) purifying the peptide of formula (4), or the peptide of formula (1), or optionally both, by RP-HPLC, wherein the peptide of formula (1) has a purity of 98%, or of 99%, or of 99.9% by weight.

2. The process of claim 1, wherein the acid-labile resin has a substitution value ranging from 0.25 to 0.35 mmole/gm.

3. The process of claim 1, wherein the polar aprotic solvent used is dimethyl formamide(DMF).

4. The process of claim 1, wherein the (X) group is selected from the group consisting of tBu, Trt, and chlorotrityl, and the (Y) group is selected from the group consisting of Trt, Tmob, Mtt, and Xan.

5. The process of claim 4, wherein the (X) group is tBu.

6. The process of claim 4, wherein the (Y) group is Trt.

7. The process of claim 1, wherein Fmoc removal is carried out in a medium comprising 0.1M-0.5M-hydroxybenzotriazole (HOBt) in 20%-50% piperidine in DMF.

* * * * *

SEQUENCE LISTING

```
<160> NUMBER OF SEQ ID NOS: 8

<210> SEQ ID NO 1
<211> LENGTH: 37
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 2, 7
<223> OTHER INFORMATION: Disulfide bridge Cys-Cys

<400> SEQUENCE: 1

Lys Cys Asn Thr Ala Thr Cys Ala Thr Gln Arg Leu Ala Asn Phe Leu
 1               5                  10                  15

Val His Ser Ser Asn Asn Phe Gly Pro Ile Leu Pro Pro Thr Asn Val
            20                  25                  30

Gly Ser Asn Thr Tyr
        35

<210> SEQ ID NO 2
<211> LENGTH: 17
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 1, 2, 11, 15
<223> OTHER INFORMATION: Amino acid has acid-labile sidechain protecting
      group that can be removed under acidic conditions
      to yield a free NH or SH group
<220> FEATURE:
<221> NAME/KEY: SITE
<222> LOCATION: 10, 14, 16, 17
<223> OTHER INFORMATION: Amino acid has acid-labile sidechain protecting
      group that can be removed under acidic conditions
      to yield a free OH group

<400> SEQUENCE: 2

Asn Asn Phe Gly Pro Ile Leu Pro Pro Thr Asn Val Gly Ser Asn Thr
 1               5                  10                  15

Tyr

<210> SEQ ID NO 3
```

```
<211> LENGTH: 19
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 1, 12, 16, 18, 19
<223> OTHER INFORMATION: Amino acid has acid-labile sidechain protecting
      group that can be removed under acidic conditions
      to yield a free OH group
<220> FEATURE:
<221> NAME/KEY: SITE
<222> LOCATION: 2
<223> OTHER INFORMATION: Amino acid is a pseudoproline serine-derived
      oxazolidine
<220> FEATURE:
<221> NAME/KEY: SITE
<222> LOCATION: 3, 4, 13, 17
<223> OTHER INFORMATION: Amino acid has acid-labile sidechain protecting
      group that can be removed under acidic conditions
      to yield a free NH or SH group

<400> SEQUENCE: 3

Ser Ser Asn Asn Phe Gly Pro Ile Leu Pro Pro Thr Asn Val Gly Ser
1               5                   10                  15

Asn Thr Tyr

<210> SEQ ID NO 4
<211> LENGTH: 37
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 1
<223> OTHER INFORMATION: Lys = Lysine t-butyloxycarbonyl
<220> FEATURE:
<221> NAME/KEY: SITE
<222> LOCATION: 2, 3, 7, 10, 14, 18, 21, 22, 31, 35
<223> OTHER INFORMATION: Amino acid has acid-labile sidechain protecting
      group that can be removed under acidic conditions
      to yield a free NH or SH group
<220> FEATURE:
<221> NAME/KEY: SITE
<222> LOCATION: 4, 6, 9, 19, 30, 34, 36, 37
<223> OTHER INFORMATION: Amino acid has acid-labile sidechain protecting
      group that can be removed under acidic conditions
      to yield a free OH group
<220> FEATURE:
<221> NAME/KEY: SITE
<222> LOCATION: 11
<223> OTHER INFORMATION: Arg = Arginine 2,2,4,6,7-pentamethyl-
      dihydrobenzofuran-5-sulfonyl
<220> FEATURE:
<221> NAME/KEY: SITE
<222> LOCATION: 20
<223> OTHER INFORMATION: Ser = a pseudoproline serine-derived
      oxazolidine

<400> SEQUENCE: 4

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
            20                  25                  30

Gly Ser Asn Thr Tyr
        35

<210> SEQ ID NO 5
<211> LENGTH: 37
<212> TYPE: PRT
```

```
<213> ORGANISM: Artificial Sequence
<220> FEATURE:
<223> OTHER INFORMATION: A synthetic peptide

<400> SEQUENCE: 5

Lys Cys Asn Thr Ala Thr Cys Ala Thr Gln Arg Leu Ala Asn Phe Leu
 1               5                  10                  15

Val His Ser Ser Asn Asn Phe Gly Pro Ile Leu Pro Pro Thr Asn Val
             20                  25                  30

Gly Ser Asn Thr Tyr
         35

<210> SEQ ID NO 6
<211> LENGTH: 37
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 1
<223> OTHER INFORMATION: Lys = Lysine t-butyloxycarbonyl
<220> FEATURE:
<221> NAME/KEY: SITE
<222> LOCATION: 2, 3, 7, 10, 14, 18, 22, 31, 35
<223> OTHER INFORMATION: Amino Acid has trityl or triphenylmethyl
      sidechain blocker group
<220> FEATURE:
<221> NAME/KEY: SITE
<222> LOCATION: 4, 6, 9, 19, 21, 30, 34, 36, 37
<223> OTHER INFORMATION: Amino Acid has tert-butyl protecting group
<220> FEATURE:
<221> NAME/KEY: SITE
<222> LOCATION: 11
<223> OTHER INFORMATION: Arg = arginine 2,2,4,6,7-pentamethyl-
      dihydrobenzofuran-5-sulfonyl
<220> FEATURE:
<221> NAME/KEY: SITE
<222> LOCATION: 20
<223> OTHER INFORMATION: Ser = a pseudoproline serine-derived
      oxazolidine

<400> SEQUENCE: 6

Lys Cys Asn Thr Ala Thr Cys Ala Thr Gln Arg Leu Ala Asn Phe Leu
 1               5                  10                  15

Val His Ser Ser Asn Asn Phe Gly Pro Ile Leu Pro Pro Thr Asn Val
             20                  25                  30

Gly Ser Asn Thr Tyr
         35

<210> SEQ ID NO 7
<211> LENGTH: 12
<212> TYPE: PRT
<213> ORGANISM: Artificial Sequence
<220> FEATURE:
<223> OTHER INFORMATION: A synthetic peptide

<400> SEQUENCE: 7

Arg Tyr Tyr Arg Trp Lys Lys Lys Lys Lys Lys
 1               5                  10

<210> SEQ ID NO 8
<211> LENGTH: 19
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
```

-continued

```
<222> LOCATION: 1, 3, 12, 16, 18, 19
<223> OTHER INFORMATION: Amino Acid has tert-butyl protecting group
<220> FEATURE:
<221> NAME/KEY: SITE
<222> LOCATION: 2
<223> OTHER INFORMATION: Ser = a pseudoproline serine-derived
      oxazolidine
<220> FEATURE:
<221> NAME/KEY: SITE
<222> LOCATION: 4, 13, 17
<223> OTHER INFORMATION: Amino Acid has trityl or triphenylmethyl
      sidechain blocker group

<400> SEQUENCE: 8

Ser Ser Asn Asn Phe Gly Pro Ile Leu Pro Pro Thr Asn Val Gly Ser
 1               5                  10                  15

Asn Thr Tyr
```